United States Patent [19]

Nakamura

[11] Patent Number: 5,242,142
[45] Date of Patent: Sep. 7, 1993

[54] COUNTERBALANCED PARALLEL LINKAGE SUPPORTING MECHANISM

[75] Inventor: Katsushige Nakamura, Hachiohji, Japan

[73] Assignee: Mitaka Kohki Co., Ltd., Tokyo, Japan

[21] Appl. No.: 629,942

[22] Filed: Dec. 19, 1990

[30] Foreign Application Priority Data

Apr. 11, 1990 [JP] Japan ................................ 2-94165

[51] Int. Cl.$^5$ ............................................ F16M 11/00
[52] U.S. Cl. ............................ 248/280.1; 248/281.1
[58] Field of Search ............ 248/280.1, 281.1, 278, 248/364

[56] References Cited

U.S. PATENT DOCUMENTS

| 4,344,595 | 8/1982 | Heller et al. ............. 248/280.1 X |
| 4,592,526 | 6/1986 | Kobelt .......................... 248/278 |
| 4,976,450 | 12/1990 | Ellefson ................. 248/280.1 X |

FOREIGN PATENT DOCUMENTS

| 23003 | 1/1981 | European Pat. Off. ........ 248/280.1 |
| 742471 | 12/1932 | France ............................. 248/278 |
| 64-56409 | 3/1989 | Japan. | |
| 99707 | 4/1940 | Sweden ........................ 248/280.1 |

Primary Examiner—David L. Talbott
Attorney, Agent, or Firm—Lowe, Price, LeBlanc & Becker

[57] ABSTRACT

Counterbalanced parallel linkage supporting mechanism comprising a pair of interlocked parallel links, each provided on the opposite side of the center shaft, a weight supported on one of the parallel links, a counterweight supported on another parallel link for counterbalancing the weight, and a shaft bushing provided on a center shaft for pivotably supporting the center shaft, the shaft bushing supported pivotably about a horizontal axis orthogonal to a center shaft.

2 Claims, 4 Drawing Sheets

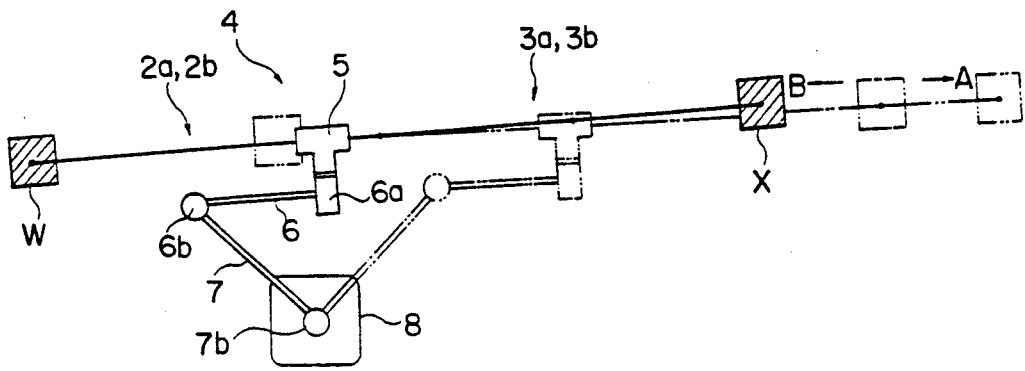
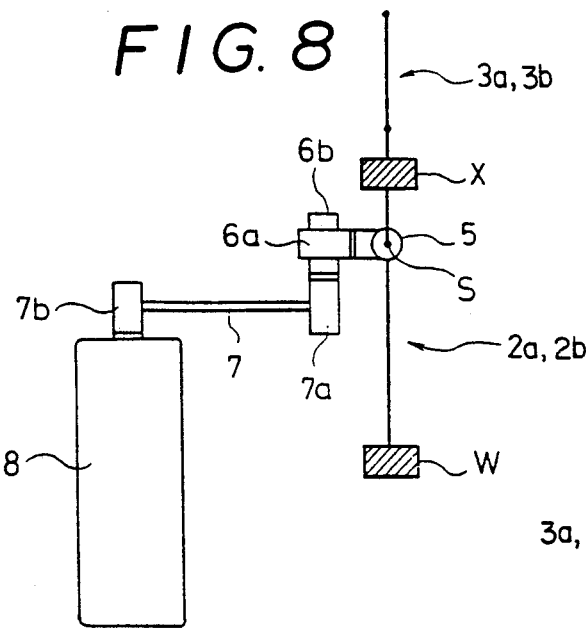
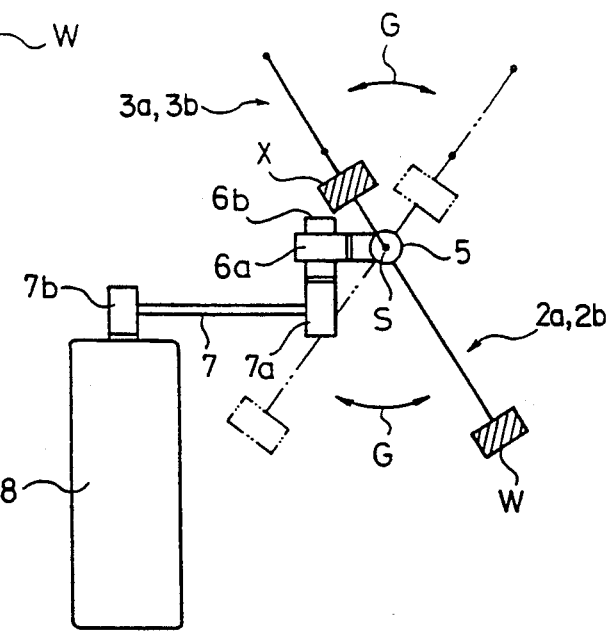

COUNTERBALANCED PARALLEL LINKAGE SUPPORTING MECHANISM

BACKGROUND OF THE INVENTION

1. Field of the Invention

This invention relates to a mechanism for supporting a parallel linkage which is generally known as a counterbalanced parallel linkage having counterweights for supporting a weighty equipment or the like in the air.

2. Description of the Prior Art

The applicant of the present invention has previously proposed a Stand Mechanism for a Medical Optical Equipment disclosed in Japanese Patent Laid-Open Publication No. 56409/1989 showing a mechanism of the conventional counterbalanced parallel linkage. That stand mechanism comprises a counterbalanced parallel linkage having a pair of parallel links, each configuration having been transformed linked with each other, and supports a weighty medical optical equipment. This conventional counterbalanced parallel linkage and the supporting mechanism thereof have been capable of performing the following four types of motion:

1. changing the supporting angle of the weight in the lateral direction (transformation of the parallel linkage);
2. motion of the weight in the up and down directions (vertical motion of the parallel linkage);
3. changing the supporting angle of the weight in left and right directions (pivotal motion about the center shaft of the parallel linkage);
4. motion of the weight within a horizontal plane in both back and forth and right and left directions (horizontal motion of the parallel linkage)

SUMMARY OF THE INVENTION

The supporting mechanism for the conventional counterbalanced parallel linkage, however, has needed at least two counterweights, the first counterweight for the above-mentioned 1 and 3 motions, and the second counterweight for the above-mentioned 2 motion, so that naturally, all the components of the parallel linkage and the supporting mechanism for supporting the parallel linkage in total have been inevitably heavy. Especially, the second counterweight for the motion of the above 2, which is for lifting vertically up and down the whole components of the parallel linkage together with the weight, tends to be quite heavy. Therefore, conventionally, it has been inconvenient to transport and assemble the components.

Accordingly, in view of the foregoing prior art, the present invention is directed to provide a supporting mechanism for a counterbalanced parallel linkage which facilitates a vertical motion (the above motion 2) of the weight without having the second counterweight as used to be provided in the prior art.

The above and other objects, advantages, features and uses will be apparent by referring to the following description when considered in connection with the accompanying drawings.

BRIEF DESCRIPTION OF THE DRAWINGS

FIG. 7 is a plan view corresponding to FIG. 5 showing the weight transferred horizontally in the lateral direction;

FIG. 8 is a front view of the parallel linkage and the supporting mechanism thereof; and FIG. 9 is a front view corresponding to FIG. 8 showing the parallel linkage pivoting about the center shaft.

DESCRIPTION OF THE PREFERRED EMBODIMENTS

Figure 1:
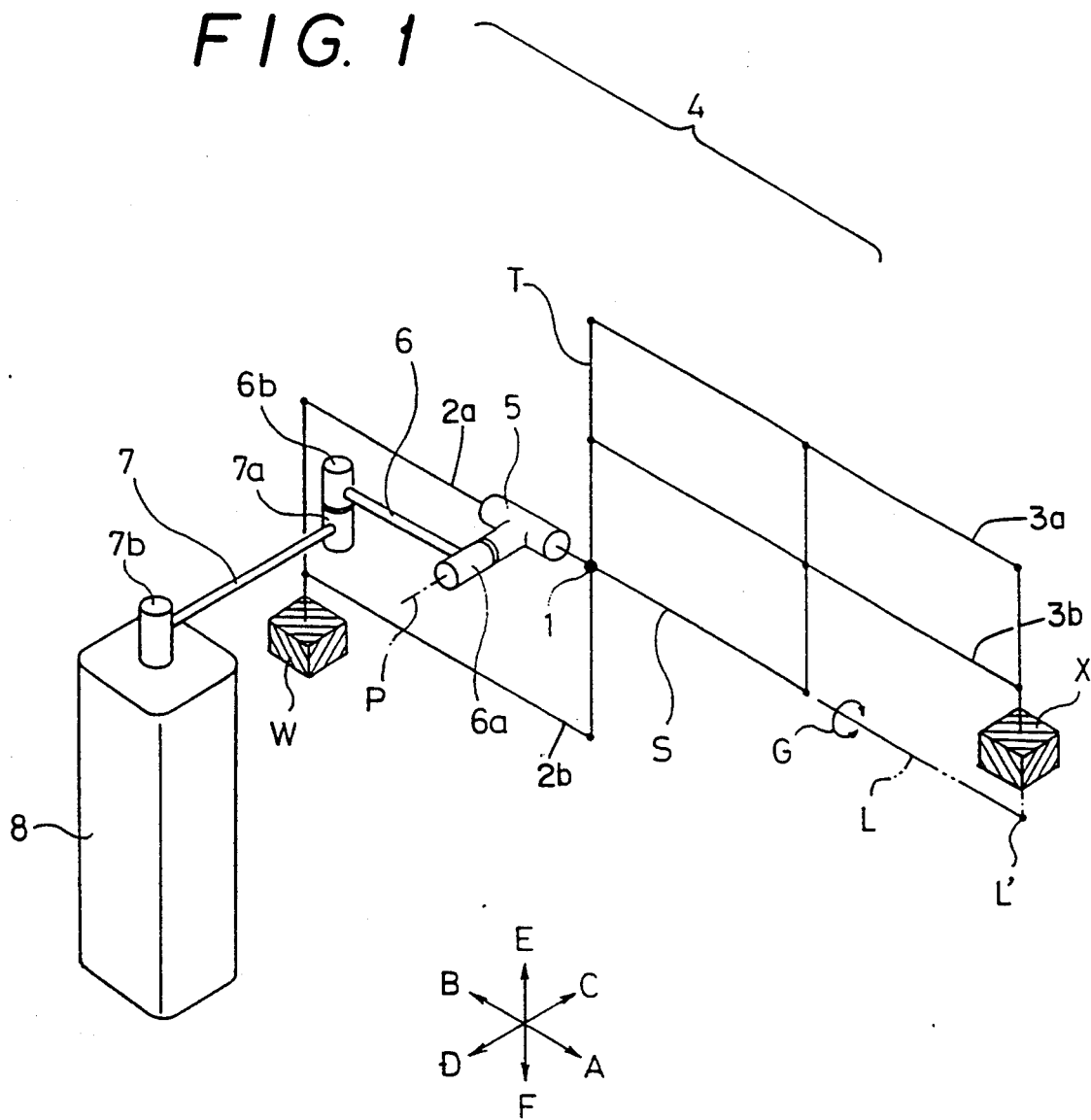
FIG. 1 is a schematic perspective view of a supporting mechanism embodying a counterbalanced parallel linkage in accordance with the present invention.

The supporting mechanism for the counterbalanced parallel linkage is provided with a shaft bushing on a center shaft of the balanced parallel linkage for pivotably supporting the center shaft, wherein the shaft bushing is supported pivotably about the horizontal axis orthogonally crossing the center shaft.

A weight "X" supported on one of the parallel links of the parallel linkage can be lifted upward or downward by rotating the whole parallel linkage about the horizontal axis provided at the shaft bushing. Thus, the parallel linkage having a single counterweight "W" is well counterbalanced even when the parallel linkage is rotated about the horizontal axis. As the weight is lifted upward or downward in this manner without lifting all of the components vertically, the second counterweight conventionally provided can be eliminated.

Referring now to the drawings, a preferred embodiment of the present invention is illustrated in FIG. 1 to FIG. 9. The directions corresponding to A, B, C, D, E and F in the drawings are referred to as front, rear, left, right, and up and down, respectively, in the description of the invention.

S shows a center shaft which pivotally supports a main frame T at a fixture point 1. In the rear side of the center shaft S, there is formed a rear parallel link 2 including the part in rear of the fixture point 1 on the center shaft S and the part lower than the fixture point 1 on the main frame T, and in the front side of the center shaft S, there is formed another front parallel link 3 including the part in front of the fixture point 1 on the center shaft S and the part upper than the fixture point 1 on the main frame T. The rear parallel links 2a and 2b and the front parallel links 3a, 3b and line S, having more members than the rear links comprise longitudinal members and lateral members, each continually maintained parallel, respectively. At the front end of the front parallel links 3a and 3b, a weight X is supported so as to position just above an extension L of the center shaft S, while, at the rear end of the rear parallel links 2a and 2b, a counterweight W is provided for counterbalancing the weight of the weight X. The front parallel link 3a and the rear parallel link 2b sharing the center shaft S and the main frame T, transform while being interlocked with each other by changing the angle formed by the center shaft S and the main frame T.

The parallel linkage 4 comprising the parallel links 2a, 2b, 3a and 3b is supported by a shaft bushing 5 provided just in the rear of the fixture point 1 on a center shaft S. More particularly, the center shaft S is pivotably supported by the shaft bushing 5, so that both pairs of the two parallel links, i.e., 2a and 2b as well as 3a and 3b, are rotatable about the center shaft S in the direction G as shown in FIG. 1. Further, the shaft bushing 5, being pivotable about a horizontal axis P crossing square with the center shaft S, is pivotably joined to an extremity 6a of the first horizontal arm 6 which is movable within the horizontal plane about a base end 6b as an axis. Furthermore, the base end 6b of the first horizontal arm 6 is pivotably joined to an extremity 7a of the second horizontal arm 7 which is movable within the horizontal plane about a base end 7b attached to a base 8.

Note that both of parallel links 3a and 3b are located above the center shaft S and that counterweight W is located thereby to be between center shaft S and the lower link 3b as best seen in FIG. 1. Also, note that link 2a is coincident with center shaft S and link 2b, relative thereto, is on the opposite side from both of links 3a and 3b. This is best seen in FIGS. 1 and 2.

The operation of the parallel linkage and the support mechanism thereof will be described hereinafter.

Figure 2:
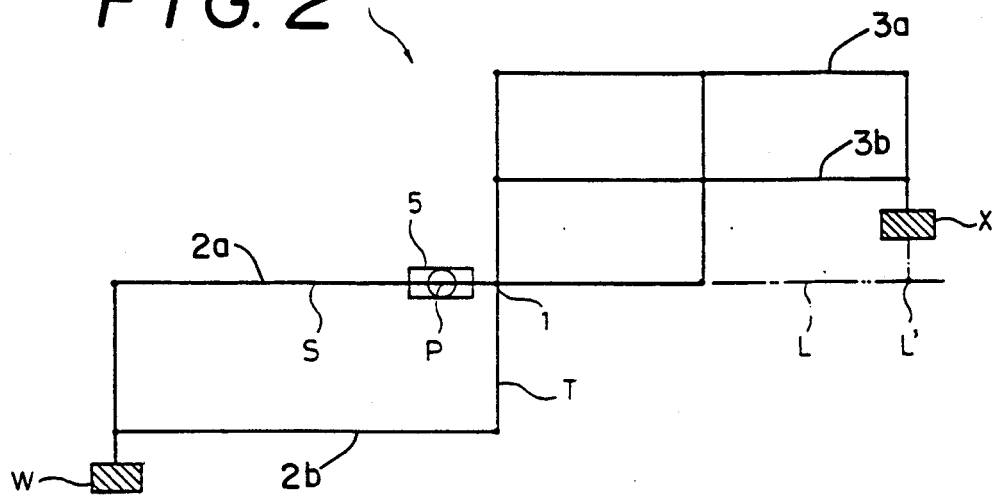
FIG. 2 is a side view of the parallel linkage.
Figure 3:
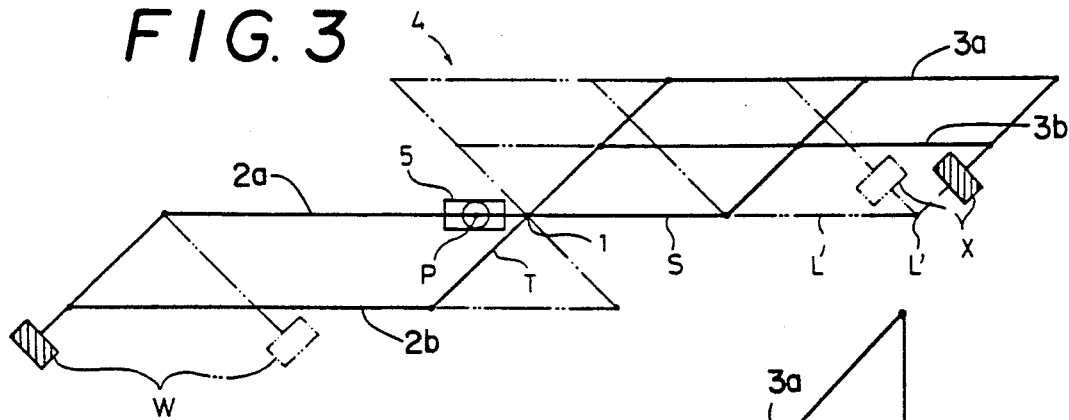
FIG. 3 is a side view corresponding to FIG. 2 showing the transformation of the parallel linkage.

(a) Change of the supporting angle by the lateral motion of the weight (FIG. 2)

The supporting angle of the weight X on the lateral plane viewed from a point L' on the extension L of the center shaft S can be varied by the transformation of a pair of interlocked parallel links. Thus, when the weight "X" is a surgical microscope or the like, the observation angle can be selectively changed with the focus upon the fixed point L'. The transformation of the parallel linkage 4 does not affect the balance maintained between the weight X and the counterweight W.

Figure 4:
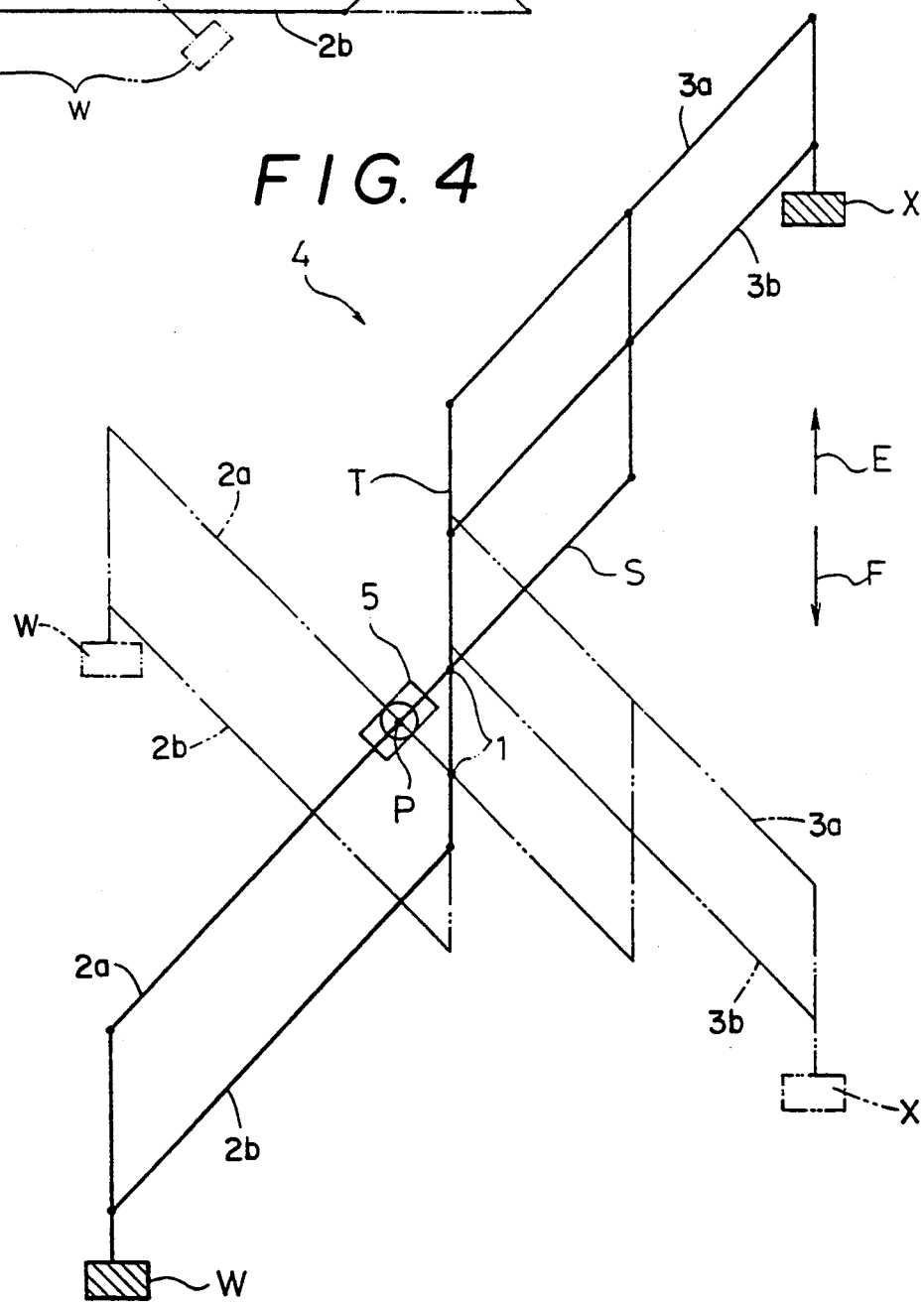
FIG. 4 is a side view corresponding to FIG. 2 showing the parallel linkage pivoting about the horizontal axis.
Figure 5:
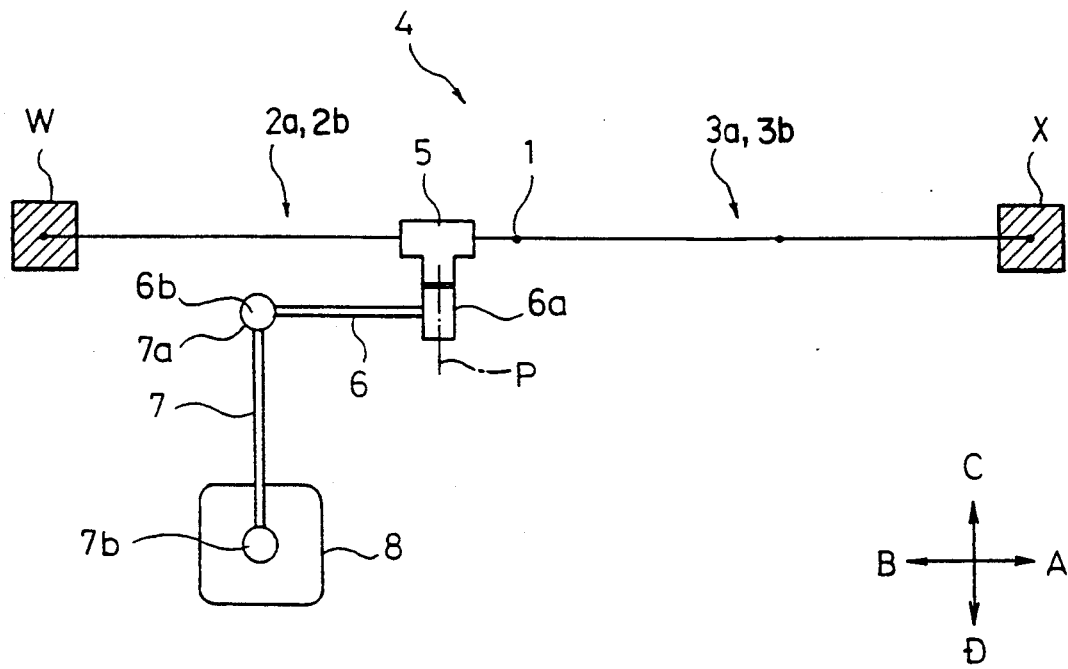
FIG. 5 is a plan view of the parallel linkage and the supporting mechanism thereof.

(b) Vertical motion of the weight (FIG. 4)

Conventionally, the vertical motion has been conducted by lifting up or lowering of the whole parallel linkage 4. However, according to the present invention, the weight X can be lifted up or down by pivoting the parallel linkage 4 about the horizontal axis P provided at the shaft bushing 5. The turning motion of the parallel linkage 4 does not affect the parallel linkage 4 being counterbalanced as a whole.

Figure 6:
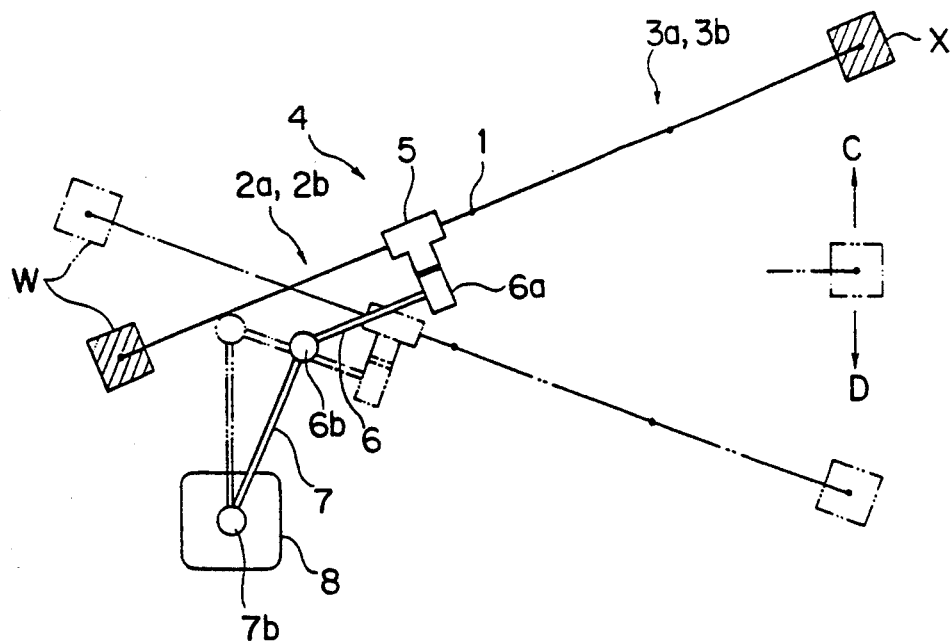
FIG. 6 is a plan view of the parallel linkage corresponding to FIG. 5 showing the weights transferred horizontally in the left and right directions.

(c) Horizontal motion of the weight (FIGS. 6 & 7)

The weight X can be translated horizontally in the left and right directions as shown in FIG. 6, and horizontally in the back and forth directions as shown in FIG. 7, by changing the crossing angle of the first and the second horizontal arms 6 and 7 or by pivoting the second horizontal arm 7 about the base 8, as the first and the second horizontal arms 6 and 7 are pivotally connected to support the whole parallel linkage 4.

(d) Change of the supporting angle by longitudinal motion of the weight (FIG. 9)

The supporting angle of the weight X in the longitudinal direction can be changed by pivoting the whole parallel linkage 4 about the center shaft S in the direction G. In this case, too, the parallel linkage 4 is kept counterbalanced.

As explained in the foregoing description, the counterbalanced parallel linkage supporting mechanism according to the present invention can transfer the weight supported on one end of the parallel link of the parallel linkage vertically upward or downward by pivoting the whole parallel linkage about the horizontal axis provided at the shaft bushing. Accordingly, as conventionally provided, there is no need for a second counterweight to lift the parallel linkage vertically upward or downward.

In this disclosure, there are shown and described only the preferred embodiments of the invention, but, as aforementioned, it is to be understood that the invention is capable of use in various other combinations and environments and is capable of changes or modifications within the scope of the inventive concept as expressed herein.

What is claimed is:

1. A counterbalanced parallel linkage supporting mechanism, comprising:

a first pair of interlocked parallel links, both provided on an upper side of a center shaft, with a first weight supported by said first pair of parallel links between said center shaft and that link of said first pair of parallel links which is closest to said center shaft; and a second pair of parallel links that is interconnected with and maintained parallel to said first pair of parallel links, one link of said second pair of parallel links being coincident with said center shaft and the second link of said second pair of parallel links being located relative thereto on an opposite side of said center shaft, supporting a counterbalancing second weight selected to counterbalance said first weight, wherein a shaft bushing is provided on said center shaft for pivotably supporting said center shaft, and said shaft bushing is supported pivotably about a horizontal axis that orthogonally crosses said center shaft.

2. The counterbalanced parallel linkage supporting mechanism as claimed in claim 1, wherein:

said shaft bushing is connected to an extremity of a first horizontal arm to be horizontally pivotable about a base end thereof; and, said base end of said first horizontal arm is horizontally pivotable as joined to an extremity of a second horizontal arm, said second arm being pivotable in a horizontal plane about a base end at which the second horizontal arm is pivotally supported upon a base.

* * * * *